(12) United States Patent
Davis (10) Patent No.: US 9,931,032 B2
(45) Date of Patent: Apr. 3, 2018

(54) SYSTEM AND METHOD FOR RETINOPATHY DETECTION

(71) Applicant: LKC Technologies, Inc., Gaithersburg, MD (US)

(72) Inventor: Charles Quentin Davis, Frederick, MD (US)

(73) Assignee: LKC TECHNOLOGIES INC., Gaithersburg, MD (US)

( * ) Notice: Subject to any disclaimer, the term of this patent is extended or adjusted under 35 U.S.C. 154(b) by 0 days.

(21) Appl. No.: 15/125,766

(22) PCT Filed: Mar. 13, 2015

(86) PCT No.: PCT/US2015/020544
§ 371 (c)(1),
(2) Date: Sep. 13, 2016

(87) PCT Pub. No.: WO2015/138963
PCT Pub. Date: Sep. 17, 2015

(65) Prior Publication Data
US 2017/0000338 A1    Jan. 5, 2017

Related U.S. Application Data

(60) Provisional application No. 61/953,409, filed on Mar. 14, 2014.

(51) Int. Cl.
*A61B 3/14* (2006.01)
*A61B 3/00* (2006.01)
(Continued)

(52) U.S. Cl.
CPC ............ *A61B 3/112* (2013.01); *A61B 3/0025* (2013.01); *A61B 3/14* (2013.01); *A61B 5/0496* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 7,438,413 | B2 * | 10/2008 | Kashiwagi | A61B 3/12 351/205 |
| 2008/0212026 | A1 * | 9/2008 | Molnar | A61B 3/14 351/206 |
| 2016/0192837 | A1 * | 7/2016 | Neice | A61B 3/112 351/206 |

OTHER PUBLICATIONS

"Preferred Practice Pattern", Diabetic Retinopathy, American Academy of Ophthalmology, 2003, 36 pp., Januar.
(Continued)

*Primary Examiner* — Mohammed Hasan
(74) *Attorney, Agent, or Firm* — Andrews Kurth Kenyon LLP; Sean S. Wooden (57) ABSTRACT

A device providing an indication of eye disease in a patient comprises a light emitter; an optical assembly arranged so that light emitted from the light emitter reaches an eye of the patient; a camera arranged to image the eye of the patient; and a controller. The controller measures the eye's pupil area using images received from the camera and adjusts the luminance of the light emitted from the light emitter as a non-constant function of the eye's pupil area so as to create a plurality of stimulus intervals. At least two of the stimulus intervals differ in their average retinal illuminance. The controller analyzes the pupil measurements and/or an electrical response in at least two of the stimulus intervals to provide an indication of eye disease based. In some embodiments, the patient's age is also used in the analysis. Methods of using said device are also contemplated.

25 Claims, 5 Drawing Sheets

(51) Int. Cl.
*A61B 3/11* (2006.01)
*A61B 5/0496* (2006.01)

(56) References Cited

OTHER PUBLICATIONS

Aiello, et al., "Diabetic Retinopathy", Diabetes Care, vol. 21, No. 1, Jan. 1998, pp. 143-156.
Antonetti, et al., "Perspectives in Diabetes, Diabetic Retinopathy, Seeing Beyond Glucose-Induced Microvascular Disease", Diabetes, vol. 55, Sep. 2006, pp. 2401-2411.
Bresnick, George H., and Palta, Mari; "Temporal Aspects of the Electroretinogram in Diabetic Retinopathy", Arch Ophthalmol, vol. 105, May 1987, pp. 660-664.
Abstract for "The pupillary light reflex in diabetes mellitus: evaluation of a newly developed infrared light reflection method", Diabetes Res., Apr. 1989, 10(4):191-5.
Faraggi, David and Reiser, Benjamin; "Estimation of the area under the ROC curve", Statistics in Medicine, 2002, 21:3093-3106, April.
Han, Young-Keun, and Ohn, Young-Hoon, "Changes of ERG Parameters in Diabetic Retinopathy", Korean Ophthalmol Soc 41:149-155, May.
Hreidarsson, A.B., Pupil Size in Insulin-dependent Diabetes, Relationship to Duration, Metabolic Control and Long-Term Manifestations, Diabetes, vol. 31, May 1982, pp. 442-448.
Holder, et al., ISCEV standard for clinical pattern electroretinography—2007 update, Doc Ophthalmol (2007) 114:111-116, May.
Hood et al., ISCEV standard for clinical multifocal electroretinography (mfERG) (2011 edition), Doc Ophthalmol (2012) 124:1-13, March.
Kjeka, et al., "Early panretinal photocoagulation for ERG-verified ischaemic central retinal vein occlusion", Acta Ophthalmologica 2013, pp. 37-41, April.
Kuroda, et al., "Pupillary light reflex in borderline diabetes mellitus", Diabetes Research and Clinical Practice, 6 (1989) 89-94.
Marmor et al., ISCEV standard for full-field clinical electroretinography—2008 update, Doc Ophthalmol (2009) 118:69-77.
Odom, et al., ISCEV standard for clinical visual evoked potentials—2009 update, Doc Ophthalmol (2010) 120:111-119.
Satoh, et al., "Photopic Electroretinogram Implicit Time in Diabetic Retinopathy", Jpn J Ophthalmol, vol. 38: 178-184, 1994.
Severns, et al., "Automated estimation of implicit time and amplitude from the flicker electroreinogram", Applied Optics, vol. 30, No. 16, Jun. 1, 1991, pp. 2106-2112.
Severns, Matthew L., and Johnson, Mary A., "Automated Implicit Time and Amplitude Determination for the 30 Hz Flicker Electroretinogram: Performance in Prediction of Neovascularization in Central Retinal Vein Occlusion", 4 pp.
Severns, Matthew L., and Johnson, Mary A., "Predicting Outcome in Central Retinal Vein Occlusion Using the Flicker Electroretinogram". Arch Ophthalmol, vol. 111, Aug. 1993, pp. 1123-1130.
Schwartz, Stephen G. and Flynn Jr., Harry W., "Pharmacotherapies for Diabetic Retinopathy: Present and Future", Hindawi Publishing Corporation, Experimental Diabetes Research, vol. 2007, Article ID 52487, 8 pp.
Straub, et al., "The Pupillary Light Reflex, 2. Prevalence of Pupillary Autonomic Neuropathy in Diabetics Using Age-Dependent and Age-Independent Pupillary Parameters,"Ophthalmologica 1992:204:143-148.
Straub, et al., "Valid parameters for investigation of the pupillary light reflex in normal and diabetic subjects shown by factor analysis and partial correlation", Diabetologia (1994) 37:414-419.
Wilkinson, et al., "Proposed International Clinical Diabetic Retinopathy and Diabetic Macular Edema Disease Severity Scales", Ophthalmology 2003; 110:1677-1682.
Ketner, et al., Abstract for "Dynamic Pupillometry in Diabetic Patients with and without Diabetic Retinopathy", Diabetic Retinopathy—Clinical Research III, 4 pp., April.

* cited by examiner

SYSTEM AND METHOD FOR RETINOPATHY DETECTION

CROSS REFERENCE TO RELATED APPLICATIONS

This application is a National Stage Application of PCT Application No. PCT/US15/20544, filed Mar. 13, 2015, entitled "System and Method for Retinopathy Detection" which claims the benefit of U.S. provisional application 61/953,409, filed Mar. 14, 2014, entitled "System And Method For Retinopathy Detection". The entirety of the aforementioned applications is incorporated herein by reference.

GOVERNMENT RIGHTS

Inventions described herein were made with government support under grant 9R44EY021121 awarded by the National Institutes of Health, USA. Accordingly, per the terms and conditions of the grant, the U.S. government has certain rights in the present application. This invention was created in part in the performance of a Cooperative Research and Development Agreement with the Department of Veterans Affairs, an agency of the U.S. government, which has certain rights in this invention.

FIELD

The present invention relates to methods and devices for detecting eye disease such as retinopathy, including retinal neuropathy and diabetic retinopathy.

BACKGROUND

Retinopathy is typically a non-inflammatory degenerative disease of the retina that may lead to visual field loss or blindness. Retinopathy can be caused by various ophthalmic conditions as well as numerous systemic diseases outside the eye, for example diabetes. Diabetic retinopathy is an eye disease that results from damage to the retina as a result of complications such as nerve damage arising from diabetes mellitus. Diabetic retinopathy affects more than 80% of all patients who have had diabetes for 10 years or more and is the leading cause of vision loss in developed countries (Aiello et al., 1998).

Many retinal disorders can be diagnosed with the aid of retinal examination. Fundus photography is a common method of determining the presence and extent of diabetic retinopathy (Wilkinson, et al. 2003). Laser photocoagulation, which has been applied in DR treatment for over half a century (Antonetti et al., 2006), is a common treatment. Laser photocoagulation is successful in arresting proliferative diabetic retinopathy (PDR) in 50% of cases. Even where further degeneration is prevented, any vision loss already incurred cannot be restored (Schwartz and Flynn, 2007).

Pupillary light reflex (PLR) refers to the dilation/constriction of the pupil in response to light reaching the retina. High intensity light on the retina results in constriction in order to reduce the total light reaching the retina, and conversely, low intensity light results in pupil dilation in order to increase the light entering the eye and reaching the retina. PLR can provide a useful diagnostic tool, allowing for testing of the sensory and motor responses of the eye. Lesions or disruptions in the eye can be detected by testing the direct response of a particular eye exposed to light entering the pupil as well as the consensual response of the eye when the opposite eye is exposed to light entering the pupil.

PLR has conventionally been used in the clinical setting to characterize the early effects of diabetic neuropathy (Hreidarsson, 1982; Devos et al., 1989; Kuroda et al., 1989). Such methods involve direct measurement of the pupil diameter or area in response to intense light. These methods, however do not change the illumination based on the pupil size and therefore provide a retinal stimulation that varies with pupil size.

Visual electrophysiology diagnostic tests such as the electroretinogram (ERG) and visual evoked potentials (VEP) are diagnostic tests used to help assess eye disease. See, for example, the textbook Principles and Practice of Clinical Electrophysiology of Vision, 2nd edition, edited by Heckenlively and Arden (2006), which describes dozens of diseases that can be diagnosed with the aid of visual electrophysiology. Standards have been developed for the most common of these tests, as described in Marmor et al. (2009), Hood et al. (2012), Holder et al. (2007), and Odom et al. (2010). As a specific example, some features of the clinical ERG are strongly correlated with diabetic retinopathy (Bresnick and Palta, 1987), (Han and Ohn, 2000) and (Satoh et al., 1994). As another example, Kjeka et al. (2013) showed greatly improved outcomes for the treatment of central retinal vein occlusion when basing treatment decisions on ERG results rather than ophthalmologic examinations alone.

Normally, ERG measurements are recorded using a large instrument (e.g., the LKC Technologies UTAS system) in a darkened room with electrodes placed directly onto the eye. Dilating drops are used to enlarge the pupil and anesthetic drops are used to numb the eye before placing the electrodes onto the eye. The eye is stimulated with light to elicit a response from the visual system which is recorded via the electrodes. The measurements are performed by a skilled technician, and the results are usually interpreted by an ophthalmologist or PhD expert in visual electrophysiology. The invasiveness and complexity described above have prevented the ERG from having widespread use in assessing diabetic retinopathy and other diseases.

The invention described in U.S. Pat. No. 7,540,613 and U.S. patent application 61/757,316, which are herein incorporated by reference, help prevent these disadvantages with ERG measurements. Nevertheless, there still exists a need for visual electrophysiology devices that are easier to use or have improved performance.

While ERG measurements have been used to assess eye disease, the combination of PLR and ERG has not been contemplated previously as a way to improve assessment of eye disease.

Effective detection and treatment of retinopathy, including diabetic retinopathy would help to minimize vision loss in affected patients.

SUMMARY

Described herein are embodiments of a device and method for providing an indication of eye disease.

An embodiment of a device to provide an indication of eye disease in a patient has a light emitter and an optical assembly arranged so that light emitted from the light emitter reaches an eye of the patient in a diffuse manner. The device also has a camera arranged to image the eye of the patient. The device also has a controller that measures the eye's pupil area using images received from the camera and adjusts the luminance of the light emitted from the light emitter as a non-constant function of the eye's pupil area so as to create a plurality of stimulus intervals. At least two of the stimulus intervals have different, nonzero, average retinal illuminances. The controller analyzes the pupil measurements in at least two of the stimulus intervals and provides an indication of eye disease based on that analysis.

In another embodiment, a method for providing an indication of eye disease in a patient is described. One step in the method includes illuminating an eye of the patient with a diffuse light stimulus having at least two stimulus intervals having different, nonzero, average retinal illuminances. Another step includes measuring the eye's pupil area and adjusting the luminance of the light as a non-constant function of the eye's pupil area. Another step includes providing an indication of eye disease based on the pupil measurements.

Electrophysiology measurements may be added to the above embodiments where the indication is provided based on both electrical and pupil measurements. Age and other factors may also be included. Conveniently, the electrophysiology measurements may be made simultaneously with at least some of the pupil measurements. Advantageously, the measurements may be performed on eyes that have not been artificially dilated, for example, with mydriatic eye drops.

In another embodiment, a device to provide an indication of eye disease in a patient has an illumination system configured to provide an eye of the patient with at least two stimulus intervals of flashes of light that differ in at least one property, the properties selected from flash frequency, flash color, background retinal illuminance, background color, and retinal illuminance energy. The device also has a controller adapted to receive and analyze an electrical signal from the visual system of the patient from at least two intervals of flashes of light so as to provide an indication of eye disease based on that analysis. The flash frequencies are between 4 Hz and 50 Hz. The retinal illuminance energies are within a factor of 1.2 of one of 1, 2, 4, 8, 10, 16, and 32 Td·s.

In another embodiment, a method for providing an indication of eye disease in a patient is described. One step includes illuminating an eye of the patient with at least two intervals of flashes of light that differ in at least one property, the properties selected from flash frequency, flash color, background retinal illuminance, background color, and retinal illuminance energy. Another step includes receiving and analyzing an electrical signal from the visual system of the patient from each interval so as to provide an indication of eye disease based on the electrical signals. The flash frequencies are between 4 Hz and 50 Hz. The retinal illuminance energies are within a factor of 1.2 of one of 1, 2, 4, 8, 10, 16, and 32 Td·s.

Pupillary measurements may be added to these last two embodiments, where the indication provided is based on both electrical and pupil measurements. Age and other factors may also be included. Conveniently, the electrophysiology measurements may be made simultaneously with at least some of the pupil measurements. Advantageously, the measurements may be performed on eyes that have not been artificially dilated, for example, with mydriatic eye drops.

BRIEF DESCRIPTION OF THE DRAWINGS

The accompanying drawings, which are incorporated in and constitute a part of this specification, illustrate several embodiments and together with the description, serve to explain the novel principles of the embodiments described herein. In the drawings.

DETAILED DESCRIPTION

Disclosed herein are embodiments of improved devices and methods to detect eye disease. These devices and methods may be used to provide an indication of visual system function of a patient. There can be an electrical circuit that controls a light stimulus directed toward the eye and a camera to monitor the pupil of the eye. The light stimulus can be modulated based on pupil measurements, for example, to reduce the variation in retinal stimulation as the pupil changes size.

Embodiments of the present invention may improve the measurements over existing devices and methods, by making the stimulation more consistent and improving the amount or type of data collected. The stimulus to the eye may comprise flashes of light or other modulated light waveforms. The stimulus to the eye may comprise a single flash of light. The stimulus to the eye may comprise a background illumination that is perceptually constant or only slowly changing. A plurality of stimuli may be used in order to assess visual system function to varying stimulus conditions.

A camera may be used to measure the pupil size so the light stimulus luminance can be adjusted as a non-constant function of the pupil size. For example, the light stimulus may be adjusted to reduce the effect of pupil size on the effective retinal stimulus. Exemplary non-constant functions include adjusting the light stimulus luminance to be related linearly to the multiplicative inverse of the eye's pupil area or related to the multiplicative inverse of the eye's pupil area through a non-linear, concave function.

The light emission may be arranged to deliver retinal illuminances that are approximately sinusoidal, triangular, or square by for example continuously modulating the light output or by delivering flashes of light in a pulse-width modulation (PWM) fashion. Alternatively, the retinal illuminances may comprise a brief flash of light once per stimulus period, or the brief flash of light may be accompanied by a background illumination that is perceptually constant.

Device measurements may include pupil responses or electrical responses. The magnitude, timing, and speed of pupil changes to visual stimulation all may be indicative of eye disease. The eye's electrical response to the visual stimulation may also be recorded and analyzed. Despite the international standard for ERG testing dictating that ERG testing should be done on patient's whose eyes have been artificially dilated, the measurements of electrical responses may be performed on eyes that have not been artificially dilated. By way of example, the time span between a flash of light and the time of the peak of the eye's electrical response may be indicative eye disease such as the degree of retinal ischemia in a patient. As another example, the peak-to-peak electrical response from the eye may be indicative of eye disease.

Combinations of the above description are also contemplated. Composition and methods of their use are contemplated. Embodiments may improve over existing devices in other ways apparent from the detailed description herein.

Definitions

In order to more clearly understand the embodiments described herein, certain terms are defined as follows. Other terms are defined in other parts of this disclosure.

The term "light emitter" refers to anything that emits electromagnetic radiation in the UV, visible, and infrared (IR) range. Exemplary light emitters include LEDs, display devices, and gas-discharge devices such as xenon flash lamps and fluorescent bulbs. In some cases herein, the term "infrared" is abbreviated as "IR".

The term "LED" refers to a light emitting diode. LED includes those comprising semiconductor, organic, and quantum-dots. The term LED includes those with integrated phosphors.

The term "patient" refers a human or other mammal from which physiological signals are to be measured. It is contemplated that the device will be placed in proximity to the patient to enable stimulation of the patient's visual system and measurement of physiological response thereto.

The term "diffuse," when referring to illumination, refers to the illumination being largely without spatial structure. Exemplary diffuse illumination can be achieved with integrating spheres, opal diffusing glass, or displays configured to produce nearly the same output over most of its pixels.

The term "retinal illuminance" refers to the product of luminance and pupil area. The unit Troland (abbreviated Td) is a measure of retinal illuminance where luminance has units of $cd/m^2$ and pupil area has units of $mm^2$.

When describing flashes of light, typically when the flash is short enough (less than about 6 ms), the eye's response is well characterized by the total energy in the flash. Thus, flashes can be characterized as having a "retinal illuminance energy" with units of Td·s, or as having a "luminance energy" with units of $cd·s/m^2$.

The term "eye disease" refers to any disease, disorder or condition which may cause, result in, or is associated with reduced vision or retinal degeneration including degeneration of the photoreceptors or neurons, for example, retinopathy. The retinopathy may be any retinopathy, including primary retinopathy or secondary retinopathy, and includes, for example, degeneration of retinal neurons, neuropathy, glaucoma, retinitis pigmentosa, central vein occlusion, branch vein occlusion, macular edema, and diabetic retinopathy. Retinopathy includes retinal gliosis, retinal degeneration or retinopathy related to neurodegenerative diseases including Parkinson's disease and Alzheimer's disease, primary retinopathies originating from the eye including retinoschisis, age-related macular degeneration and glaucoma, and secondary retinopathies originated from systemic diseases including diabetic retinopathy, hepatic retinopathy, renal retinopathy, hypertension, vascular diseases, congenital heart disease, autoimmune disorders including rheumatoid arthritis, multiple sclerosis, neurofibromatosis, Lyme neuroborreliosis, Down's syndrome, autism, sickle cell anemia, infections with HIV and cytomegalovirus, thyroid disorders, or liver disorders.

The term "or" refers to at least one member in a set being true. For example, A or B means A is true, B is true, or A and B are both true.

DESCRIPTION

Various embodiments, as well as additional objects, features, and advantages thereof, will be understood more fully from the following description.

Figure 1:
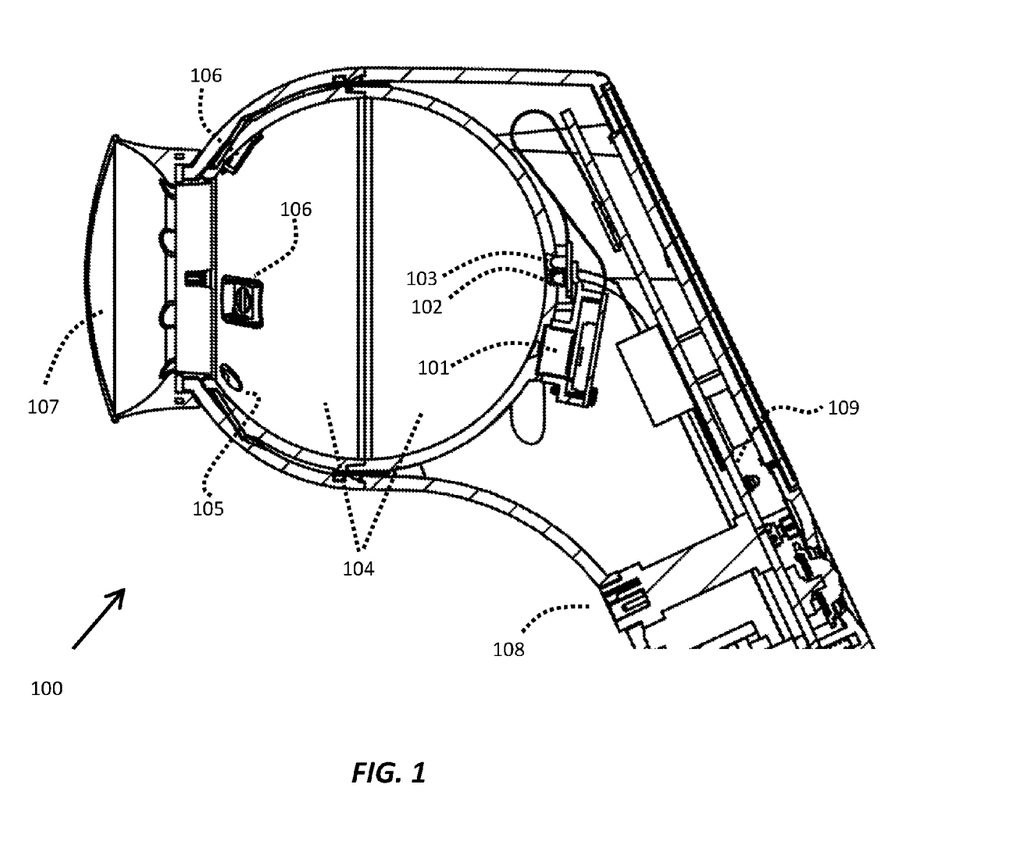
FIG. 1 is a cross sectional view of an exemplary diagnostic device.

FIG. 1 shows an exemplary device 100 used to provide an indication of visual system function of a patient. An eyecup 107 may contact the bony regions around the eye to keep the device against or near the patient. The light emitter 106 shines light into an optical assembly 104, which directs the light to the patient's eye.

In this example, the optical assembly 104 acts as an integrating sphere to deliver the light emitted from the light emitter 106 in a diffuse manner to the patient's eye. A diffuse light source enables interrogation of large portion of the retina and makes patient fixation less important. Other exemplary optical assemblies do not require light from the light emitter 106 to be reflected before reaching the patient's eye, for example, the light may be refracted, diffused, scattered, or may have a direct path between the light emitter and the patient's eye. In some embodiments optical components such as lenses, ground glass, or translucent plastic may be used in the illumination pathway between the light emitter 106 and the patient's eye. The illumination system can provide substantially even illumination (i.e., illuminated within a factor of 2 of the same illumination as calculated with a simple anatomical and optical model) to at least 30% of the retina of the eye. In some embodiments, more that 30% of the retina is illuminated, for example, 35%, 40%, 45%, 50%, 55%, 60%, 70%, 80%, or more of the retina can be substantially evenly illuminated.

The light emitter 106 may be, for example, an RGB LED, for example, a CREE CLV6Aa, an Avago ASMT-MT000-0001, or an Osram LRTD-C9TP. The light emitter 106 may be, for example, a red, green, blue, white LED such as CREE XLamp XM-L. Individual LEDs or other light sources may be used. Two components in the light emitter 106 are visible in the cross section of the device 100; two more are on the other half, for a total of four. The number of components in the light emitter 106 need not be 4; 1, 2, 3, 4, 5, 6, 7, 8, 9, 10, 11, 12 or more is contemplated. A larger number of components comprising the light emitter 106 gives improved light uniformity in the integrating sphere and a brighter possible light output; however, larger numbers are inconvenient is terms of manufacturing difficulty and cost.

As shown in FIG. 1, a camera 101 may image the patient's eye through the hole in the optical assembly 104 and the eyecup 107. The eyecup 107 may be designed to rest on regions around a patient's eye so as to reduce the amount of light originating outside of the device 100 from reaching the eye. Alternatively, the eyecup 107 may be designed not to contact the patient. An optional fixation light 102 may provide a target for the patient to fixate on during the testing process. When using an infrared light emitter 103, at least 50% of its energy will be emitted at wavelengths longer than 710 nm. The infrared light emitter 103 may be used to illuminate the patient's eye during the exposure time of the camera 101. In some embodiments, the device 100 does not have an infrared light emitter 103.

In embodiments making electrical measurements, patient connector 108 may be used to make a set of electrical connections to the patient so as to be able to receive an electrical signal from the patient. The electrical signals may be gathered from the patient using any number of electrodes (e.g., 1, 2, 3, 4, 5, 6, 7, 8, 9, 10, or more) operationally connected to the device 100 via a cable. Exemplary locations to measure the response include on the surface of the eye (e.g., with electrodes such as Burian Allen electrodes, (Hansen Labs, Coralville Iowa USA), DTL electrodes (LKC Technologies, Gaithersburg, Md.), gold foil electrodes (CH Electronics, Bromley, UK), and ERG Jet electrodes (LKC Technologies, Gaithersburg, Md.)), under the epithelium (e.g., with a needle electrode), on the skin near the eye (e.g., with LKC Sensor Strip electrodes as described in the PCT patent application WO 2014/039525), on the back or top of the head (e.g., using gold cup electrodes (e.g., Natus Neurology Inc., —Grass Products, Warwick R.I. USA)).

Figure 2:
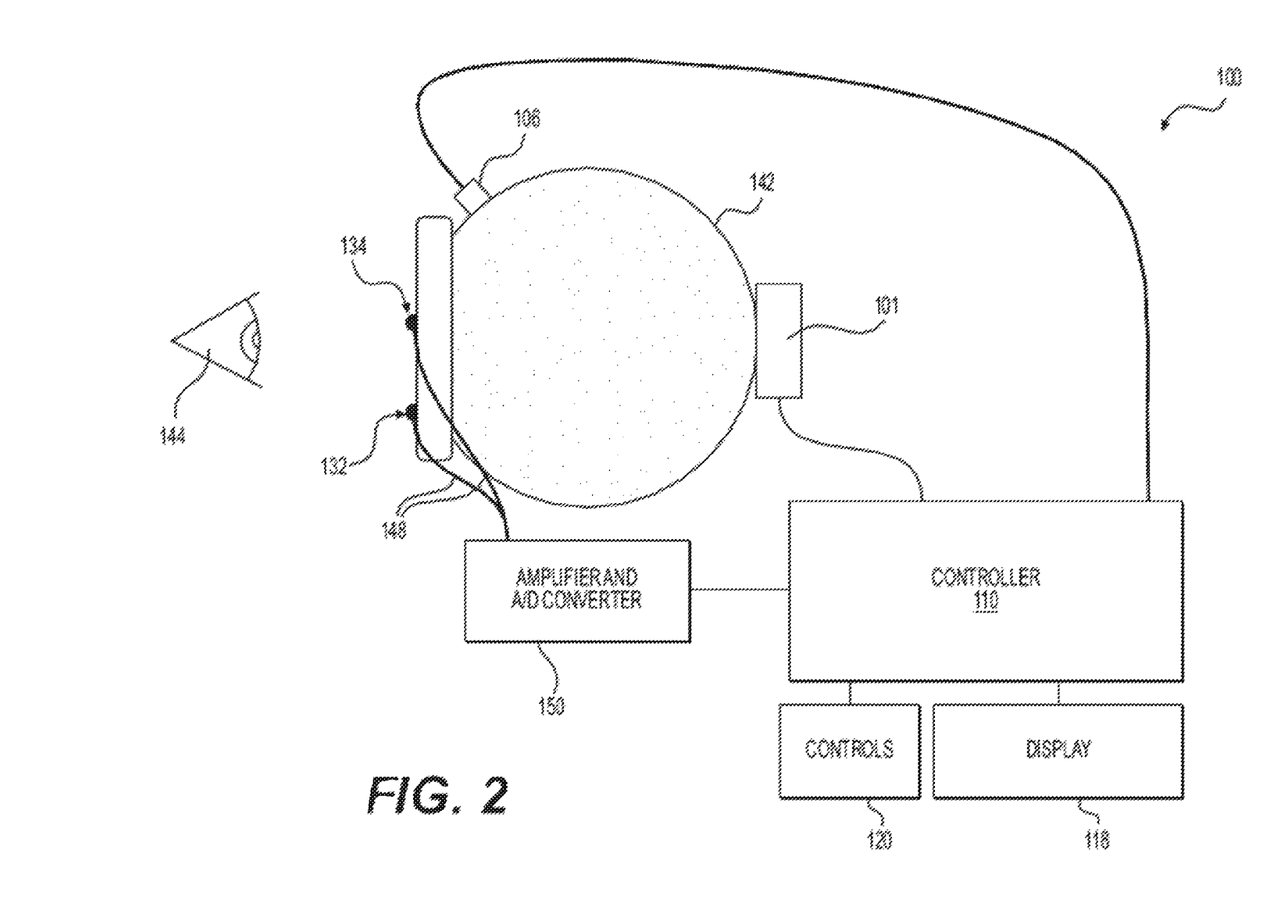
FIG. 2 is a schematic view illustrating components contained within the exemplary diagnostic device of FIG. 1

FIG. 2 depicts a schematic illustration of components that may be contained within the device 100 of FIG. 1 as previously shown in U.S. Pat. No. 7,540,613. In FIG. 2, the light emitter 106 provides a light stimulus to the eye 144. Current high brightness LED's have sufficient brightness for carrying out the present invention with an efficient diffuser, however, in certain applications a plurality of LEDs may be used for a light emitter 106.

A light emitter 106 is controlled by a controller 110 that provides the overall control of the device 100. Controller 110 may be a microcontroller or microcomputer device with a processor, memory and other connections to other components of device 100. Controller 110 may be a pre-programmed computer that is programmed to perform the functions and controls described herein. Alternatively, controller 110 may include wireless connections or wired connections that allow remote programming (e.g., for additional functions or updates). Those of ordinary skill in the art would understand how to program and operate controller 110. Control of the light emitter 106 is performed by the controller 110 which may control the timing of the firing of the light and camera sources, as well as the intensity, frequency and synchronicity thereof as further described below. By way of example, the controller 110 may modulate the activity of the light emitter 106, such as an LED to provide a series of brief flashes of light of predetermined duration, however, other stimulus waveforms or stimulus frequencies may also be utilized as further described below.

The light emitter 106 is positioned so as to emit light to the interior of a diffuse spheroidal reflector 142 so that the light from the light source is directed uniformly toward the eye 144 from all directions. In the illustrated embodiment, the diffuse spheroidal reflector 142 is spheroidal in configuration with a white interior surface to enhance the reflectivity. The white surface may be a coating (e.g., paint) or diffuse spheroidal reflector 142 may be made for example, from white plastic. The use of the diffuse spheroidal reflector 142 provides an even illumination to most of the retina of the eye 144. Diffuse spheroidal reflector 142 is an exemplary optical assembly 104.

Returning to FIG. 2, as previously explained, the light stimulus by the light emitter 106 gives rise to a pupil response and an electrical signal from the eye 144. The pupil response may be sensed by camera 101. The electrical signal may be sensed by e.g., electrodes 132, 134 contacting the skin of the patient proximate to the eye 144, whereby the electrical signal is communicated by wires 148 to an amplifier and an analog to digital (A/D) converter shown as block 150. The A/D converter (located for example on the electronics board 109 in FIG. 1) may measure the electric signals on the electrodes and provide the information to the controller 110. The controller 110 may analyze the pupil response and/or the electric signals so as to provide an indication eye disease.

The analysis of the data from the electrical signals sensed by the electrodes 132, 134 is, as described herein, carried out by the controller 110. Some algorithms for specifically assessing retinal ischemia in a patient have been published. See, for example, Severns et al. (1991), Severns and Johnson (1991), and Kjeka et al. (2013). For other diseases, some algorithms are described in the references cited in the Background section above.

As further components of the device 100, (FIG. 1) there are controls 120 that may be used to initiate each test and to enter customized settings. In addition, the device 100 may provide a visual readout 118 to the user of the results of each test, that is, the readout 118 provides a visual readout to the user that is related to the amount of retinal ischemia of the eye.

The optional amplifier and A/D converter 150 may be a biomedical amplifier using 16 bit (or more) A/D converters that eliminates gain adjustment and the prolonged recovery from saturation of conventional amplifiers. The device 100 may utilize a low gain differential amplifier (no more than 32×) and a high resolution (typically 18 bits or greater) differential A/D converter to acquire the signal from the eye 144 via the skin electrodes 132, 134. Thus, the amplifier has a very high tolerance for noise and offsets, while producing highly faithful reproduction of the input waveform. In some embodiments, the amplifier and A/D converter may be built into the same device (e.g., an ADS1220, ADS1248, ADS1292, ADS1294, ADS1298, or ADS1299 from Texas Instruments or an AD7195, AD7194, AD7193, AD7799, AD7738 from Analog Devices to name a few). Some embodiments do not use an amplifier. Input impedance of the system can be very high (>10 MΩ) so that the relatively high impedance of the electrodes 132, 134 contacting the skin does not significantly affect the results. The output of the A/D converter in block 150 can be connected to the controller 110, which analyzes the data.

Conveniently, all the electrodes used for one eye may be located in a self-adhering electrode array such as those described in PCT patent application WO 2014/039525, the disclosures of which are expressly incorporated by reference herein.

An infrared light emitter 103 may be optionally used to image the eye in the infrared spectrum. Contrast between the pupil and the iris may be improved with infrared illumination. The controller 110 may modulate a light emission from an infrared light emitter 103 to create infrared flashes of light. The duration of the infrared flashes may be constant, or may dynamically change in operation to provide varying exposures in camera 101. A typical exposure time in some embodiments may be 2.6 ms. However, the exposure time may be varied by the controller 110, for example, based on feedback from sensors.

Generally, a shorter exposure time may be better because images have less motion blur and are less affected by external light, but shorter exposure times also increase the peak electrical power demands of the device 100 and provide less light to the camera 101.

An electronics board 109 may have a controller 110 may modulate a light emission from the light emitter to create a light stimulus having a stimulus frequency between 4 Hz and 50 Hz, including between 20 Hz and 40 Hz. These frequencies enable an electrical response to the changing light to be measured simultaneously to pupil measurements that are above the fusion frequency for the pupil reflex. Frequencies higher than 50 Hz may be used to provide perceptually constant light. Frequencies lower than 4 Hz may be used to measure a dynamic pupil or electrical response.

In some cases, controlling the timing between the stimulus frequency and the infrared flash frequency may be advantageous so that, for example, the lighting created by the light stimulus interacts in a consistent manner with the infrared flashes. Other potential advantages of controlling the timing between the two frequencies include reduced peak power, better contrast with less chromatic aberration and less changes to lighting levels in embodiments using a camera sensitive to visible and IR light. Without time synchronization, lighting levels in embodiments using a camera sensitive to visible and IR light will vary at the beat frequency between the visible and infrared light frequencies.

The light emitter 106 generates visible light that may stimulate the visual system of a patient. In some embodiments, the light emitter 106 creates a light stimulus that occurs on a periodic basis having a stimulus frequency within 0.01 Hz of one of the following frequencies: 26.94, 27.13, 27.32, 27.51, 27.70, 27.90, 28.10, 28.31, 28.51, 28.72, 28.94, 29.15, 29.37, 29.59, 29.82, 30.05, 30.28, 30.52, 30.76, 31.00, 31.25, 31.50, 31.76, 32.02, 32.28, 32.55, 32.83, 33.10, 33.67 Hz, or integer multiples thereof. Other frequencies may be used. Different stimulus intervals may use the same or different stimulus frequencies.

In some embodiments, the light emitter 106 creates a light stimulus having a stimulus frequency within 0.1 Hz of 28.31, 28.72, or 32.55 Hz, or integer multiples thereof. In other embodiments, the light emitter 106 creates flashes at a frequency above about 50 Hz and additional light at a frequency lower than 40 Hz, creating the appearance of a flickering light on top of a constant background. For example, the device 100 may create a flickering light at a frequency within 0.01 Hz of 28.31 Hz and a perceptually-constant background at a frequency within 0.1 Hz of 283.06 Hz. In some embodiments, the light emitter 106 generates a light stimulus having a stimulus frequency greater than 7 Hz.

A nonzero retinal background illuminance may be used in none, some, or all intervals. For example, the ISCEV ERG standard (Marmor et al. (2009)) recommends a nonzero background luminance to reduce the effect of rods in certain tests. The flash frequency is another method to reduce the effect of rods on the measured response, as the critical fusion frequency for rods is lower than that of cones.

The flash and background (if present) color is contemplated to be white or non-white. White flashes and backgrounds can be synthesized from red, green, and blue light emitters, or they can be emitted by for example a white LED. Colored stimuli may be useful for stimulating certain photoreceptors more than other photoreceptors.

In embodiments, the light stimulus can be a non-constant function of the pupil area, which is to say that the luminance stimulus emitted by the device changes based on the measured pupil area.

Figure 3A:
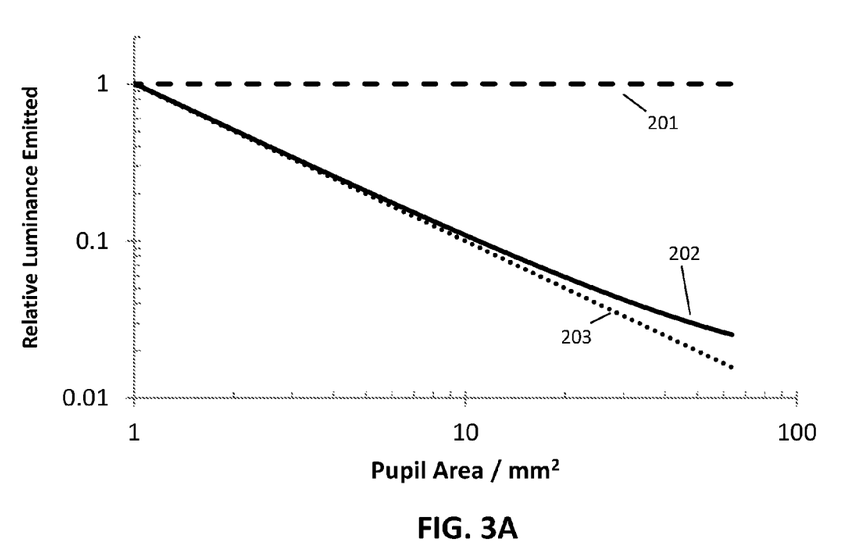
FIG. 3 shows three exemplary relations between luminance and pupil area, from the perspective of luminance emitted from an exemplary diagnostic device (FIG. 3A) and of retinal illuminance (FIG. 3B).
Figure 3B:
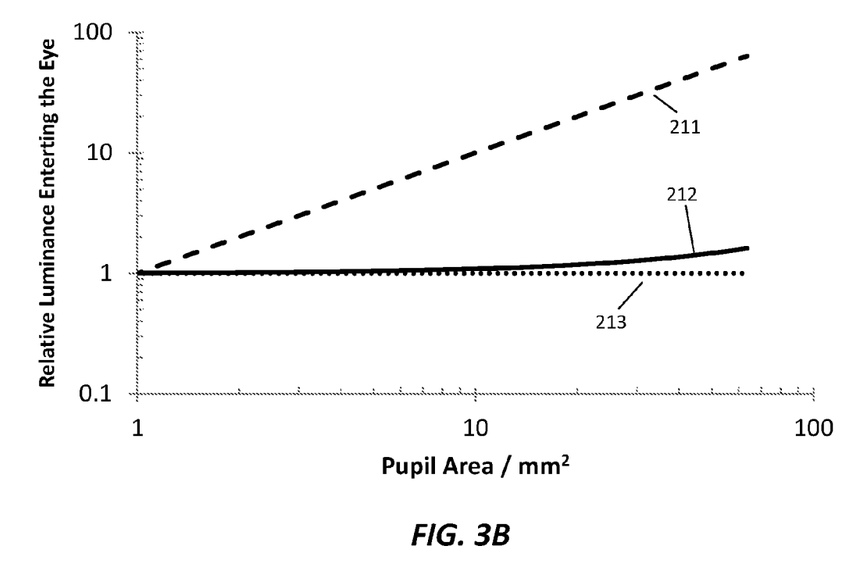

Exemplary relations between luminance of the visual stimulus and the pupil area are shown in FIG. 3, where FIG. 3A shows the relation between the light emitted from the device 100 and pupil area; FIG. 3B shows the relation between retinal illuminance and pupil area. Curve 201 shows a flash luminance that is independent of pupil area. In this case, as shown by Curve 211, the total amount of light entering the eye changes linearly with pupil area. In some embodiments, the light stimulus may be linearly related to the multiplicative inverse of the eye's pupil area. For example, the light stimulus may be made so that the energy entering the eye is constant, independent of pupil size. Curves 203 and 213 show this relation, where the amount of light entering the eye is constant.

In other embodiments, the light stimulus may be related to the multiplicative inverse of the eye's pupil area through a non-linear, concave function. Using a non-linear concave function may compensate for the eye's reduced sensitivity to light entering away from the center of the pupil (e.g., the Stiles-Crawford effect). In these cases, the amount the light is reduced as the area increases is smaller than the amount that the pupil area increased. Curves 202 and 212 show this relation, where the amount of light entering the eye increases slowly with pupil area, as the effectiveness of stimulating the retina is reduced for light not entering the center of the pupil.

The controller 110 in the electronics board 109 may be any of those known in the art. The controller 110 may be a single microprocessor, for example, one sold by Analog Devices, Atmel, Intel, Microchip, Texas Instruments, etc. Alternatively, the controller 110 may be distributed among many integrated circuits on one or more printed circuit boards in the device 100. The controller 110 may be configured to modulate the light output of a light emitter and to receive and analyze the electrical signal from a patient.

In some embodiments, the controller 110 may communicate with a camera and measure the pupil size in images taken with the camera. In some embodiments, the controller 110 may modulate the light output from additional light emitters, such as a second light emitter, a third light emitter, or an infrared light emitter. The controller 110 may provide to the operator an indication of eye disease in a human using a display or providing a means to communicate the information to a computer or other electronic device.

Embodiments may improve over existing visual electrophysiology devices. An illumination system may provide two intervals of flashes of light that differ in at least one property, selected from flash frequency, flash color, background retinal illuminance, background color, and retinal illuminance energy. An advantage in using multiple intervals of stimulation is they provide an internal control. Variables such as electrode placement and certain stimulation errors can be partially compensated for by examining multiple intervals having different visual stimulations.

Satoh et al. (1994) tested 3 different flash luminance energies (3.28 cd·s/m$^2$, 1.04 cd·s/m$^2$, and 0.328 cd·s/m$^2$). While their data showed a difference in average (across individuals) the implicit time between the flash of light and the eye's electrical response, they did not describe a difference in timing for an individual nor did they describe that using more than one intensity could be useful. Satoh et al. fully dilated their subjects, as recommended by the international standard (Marmor et al., 2009); however, this practice prevents measuring a pupillary response.

The devices and methods disclosed herein can be used to detect vision threatening diabetic retinopathy. As shown in Bresnick and Palta (1987), Han and Ohn (2000) and Satoh et al. (1994), the implicit time of the 30 Hz flicker ERG test correlates with diabetic retinopathy. These researchers all artificially dilated their patients before measuring their ERG. The American Academy of Ophthalmology (AAO, 2003) recommends treatment of severe non-proliferative diabetic retinopathy or worse (herein, "vision threatening diabetic retinopathy"). As described herein, using at least two intervals of visual stimulation may have improved performance for detecting vision-threatening diabetic retinopathy.

A controller in the device may measure the pupillary response or the electrical response from the visual system of the patient being tested and provide an indication of visual system performance. The flash frequencies can be between 4 and 50 Hz. The retinal illuminance energies for both intervals can be within a factor of 1.2 of one of 1, 2, 4, 8, 16, and 32 Td·s. Retinal illuminance energies less than 1 Td·s create very small electrical responses that may be difficult to accurately measure. Retinal illuminance energies greater than 32 Td·s may be annoyingly bright to some patients.

In some embodiments, both intervals use retinal illuminance energies that are within a factor of 1.2 of one of 4, 8, 16, or 32 Td·s. In some embodiments, both intervals use retinal illuminance energies that are within a factor of 1.2 of one of 4 or 8 Td·s. In some embodiments, both intervals use retinal illuminance energies that are within a factor of 1.2 of one of 4 or 16 Td·s. In some embodiments, both intervals use retinal illuminance energies that are within a factor of 1.2 of one of 4 or 32 Td·s. In some embodiments, both intervals use retinal illuminance energies that are within a factor of 1.2 of one of 8 or 16 Td·s. In some embodiments, both intervals use retinal illuminance energies that are within a factor of 1.2 of one of 8 or 32 Td·s. In some embodiments, both intervals use retinal illuminance energies that are within a factor of 1.2 of one of 16 or 32 Td·s.

In some embodiments, the illumination system provides three intervals of flashes of light, each interval having a retinal illuminance energy within a factor of 1.2 of one of 1, 2, 4, 8, 16, and 32 Td·s. In some embodiments, the three intervals each have a retinal illuminance energy within a factor of 1.2 of one of 4, 8, 16, or 32 Td·s. In some embodiments, the three intervals each have a retinal illuminance energy within a factor of 1.2 of one of 4, 8, or 16 Td·s. In some embodiments, the three intervals each have a retinal illuminance energy within a factor of 1.2 of one of 4, 8, or 32 Td·s. In some embodiments, the three intervals each have a retinal illuminance energy within a factor of 1.2 of one of 4, 16, or 32 Td·s. In some embodiments, the three intervals each have a retinal illuminance energy within a factor of 1.2 of one of 8, 16, or 32 Td·s.

In some embodiments, the illumination system provides four intervals of flashes of light, each interval having a retinal illuminance energy within a factor of 1.2 of one of 1, 2, 4, 8, 16, and 32 Td·s. In some embodiments, the four intervals each have a retinal illuminance energy within a factor of 1.2 of one of 4, 8, 16, or 32 Td·s.

In some embodiments, the controller 110 measures the eye's pupil area using images received from the camera 101 and adjusts the luminance of the light emitted from the light emitter 106 as a non-constant function of the eye's pupil area so as to create a plurality of stimulus intervals. At least two of these stimulus intervals may differ in their average retinal illuminance, in order to measure the pupil's response to the differing stimuli. Some potential metrics for the pupil response include its area or diameter (maximum, minimum, average, ratio, fractional change, etc.) in some part of the two or more stimulus intervals, its contraction velocity from a dimmer retinal illuminance to a brighter retinal illuminance, its dilation velocity from a brighter to dimmer retinal illuminance, the amplitude of unrest, the area under the curve of pupillary unrest, the period of the pupillary unrest, the latency time of the pupillary light reflex, or the fusion frequency for the pupillary response. See, for example, Straub (1994) for a detailed description of some of these metrics.

In some embodiments, the at least two stimulus intervals include a first stimulus interval whose average retinal illuminance is between 10 Td and 200 Td and a second stimulus interval whose average retinal illuminance is between 400 Td and 2000 Td. For example, the first stimulus interval has an average retinal illuminance between 40 Td and 200 Td. For flashes of light (e.g., flickering light), the average retinal illuminance equals the product of the retinal illuminance energy and the flash frequency. For example, if the retinal illuminance energy of the flashes in 28.3 Hz flickering light is 32 Td·s, then the average retinal illuminance is 905.6 Td. The at least two stimulus intervals may both have durations between 1 second and 120 seconds, for example, between 1 second and 30 seconds or between 2 seconds and 20 seconds or between 5 and 15 seconds. In some embodiments, the length of the intervals may vary based on an analysis of the electrical response. If the uncertainty in the electrical response is small, a shorter duration may be used in comparison to when the uncertainty in electrical response is larger.

In some embodiments, two stimulus intervals are repeated two or more times to enable repeated measurements for improved precision and error estimation. In some embodiments, the number of replicates is variable based on the error estimation.

Some embodiments use a combination of metrics to provide an indication of eye disease in a patient. Even if the metrics are known independently to correlate with disease or the other metrics, there is no a-priori guarantee of improved results using combinations. For example, Straub (1994) found many metrics of pupil response to differ between diabetics and normal individuals. However, most were correlated with each other and therefore provided no additional diagnostic information. Severns and Johnson (1993) found that while the implicit time of the 30 Hz flicker electroretinogram was correlated with central retinal vein occlusion (CRVO) and that the implicit time was also age dependent, the combination of age and implicit time did not statistically significantly improve the diagnostic performance in detecting CRVO. As shown in the examples below, with the novel stimuli described herein, many combinations of pupil and electrical measurements and patient age show improved performance compared to sub-combinations.

Exemplary eye diseases include retinitis, optic neuritis, macular degeneration, diabetic retinopathy, proliferative diabetic retinopathy, nonproliferative diabetic retinopathy, diabetic macular edema, progressive retinal atrophy, progressive retinal degeneration, sudden acquired retinal degeneration, immune-mediated retinopathy, retinal dysplasia, chorioretinitis, retinal ischemia, retinal hemorrhage, hypertensive retinopathy, retinal inflammation, retinal edema, retinoblastoma, central retinal vein occlusion, branch retinal vein occlusion, or retinitis pigmentosa. For example, the eye disease may be is diabetic retinopathy or diabetic macular edema.

While the above descriptions have emphasized compositions, methods of their use are also contemplated. To provide an indication of eye disease, the methods involve illuminating an eye of the patient with a diffuse light stimulus having at least two stimulus intervals having different, nonzero, average retinal illuminance. The methods also involve measuring the eye's pupil area and adjusting the luminance of the light as a non-constant function of the eye's pupil area. The methods also involve providing an indication of eye disease based on the pupil measurements. Electrical responses measured from the visual system and the patient's age may also be used in the analysis to provide an indication of eye disease.

In some embodiments the function is linearly related to the multiplicative inverse of the pupil area. In other embodiments, the function is a non-linear, concave function of the multiplicative inverse of the pupil area.

The methods to provide an indication of eye disease may include at least two stimulus intervals comprises flickering light having a flicker frequency between 4 Hz and 50 Hz, for example, between 20 Hz and 40 Hz. The at least two stimulus intervals both may have a duration between 1 second and 30 seconds, for example, between 2 seconds and 20 seconds. The at least two stimulus intervals include a first stimulus interval whose average retinal illuminance may be between 10 Td and 200 Td and a second stimulus interval whose average retinal illuminance may be between 400 Td and 2000 Td. For example, the first stimulus interval may have an average retinal illuminance between 40 Td and 200 Td.

The methods may further include receiving and analyzing an electrical signal from the visual system of the patient and wherein the indication is based analysis of the electrical signal and the pupil measurements. Conveniently, in some embodiments there may be at least one stimulus interval whose pupil measurements and electrical signals are both used in the analysis for the indication of eye disease, which, for example, may reduce the testing time.

EXAMPLES

Example 1: Measurements of Implicit Times in Humans

Figure 4:
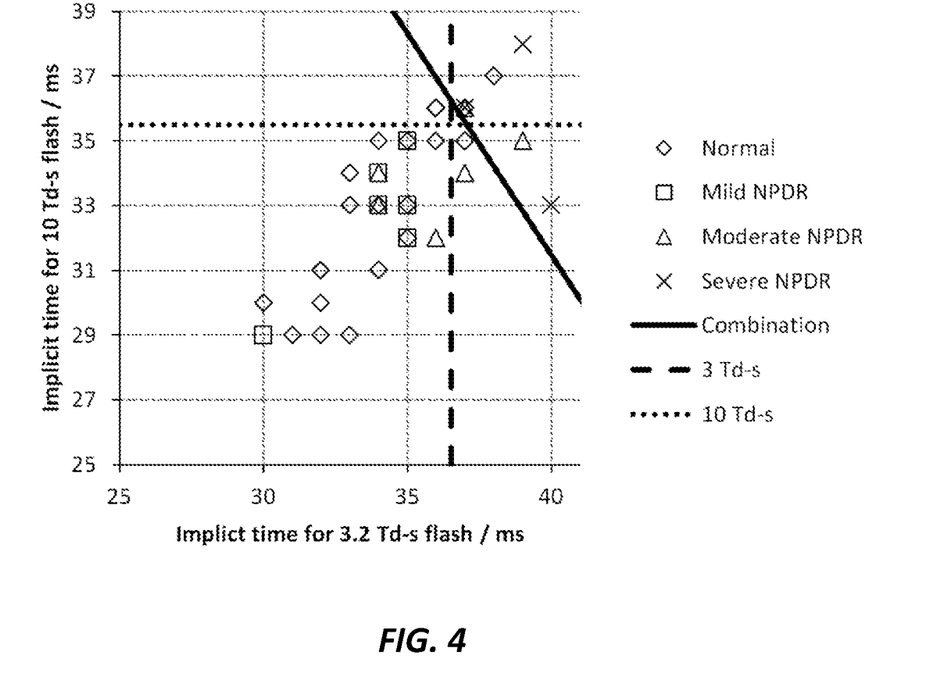
FIG. 4 shows exemplary clinical data. The x-axis shows the ERG flicker implicit time for with a 3.2 Td·s stimulus. The y-axis shows the ERG flicker implicit time for with a 10 Td·s stimulus. The symbols represent individual eyes from subjects with varying levels of diabetic retinopathy. The lines show possible thresholds to use for the detection of vision-threatening diabetic retinopathy.

Using an IRB-approved protocol, 36 humans were tested with 4 illumination levels with a 30 Hz flickering light, including 1, 3.2, 10, and 32 Td-s. FIG. 4 shows a scatterplot of the results for the 3.2 Td-s data and 10 Td-s data, where the implicit time is plotted. The implicit time is the time delay between the flash of light and the electrical response. Here, we analyze the time delay to the peak of the fundamental of the response (Severns et al 1991); others use the time delay to the peak of the waveform (Marmor et al. 2009). From these data, an indication of visual function can be obtained. The subjects were not artificially dilated.

Example 2: Detecting Diabetic Retinopathy

The humans tested in Example 1 were categorized in terms of their level of diabetic retinopathy through clinical assessment. Of the 36 humans, 2 had vision-threatening diabetic retinopathy (severe NPDR). Severe non-proliferative diabetic retinopathy (NPDR) is the mildest form of vision-threatening diabetic retinopathy (VTDR). The goal is to differentiate VTDR (i.e., severe NPDR and worse) from moderate NPDR, mild NPDR, and diabetics without retinopathy (normal). Prior art methods such as Bresnick and Palta (1987), Han and Ohn (2000) and Satoh et al. (1994) created a cutoff between diseased and healthy using one stimulus condition, dilated pupils, and illumination that was not adjusted by pupil size measurements. The dashed and dotted lines in FIG. 4 use only one stimulus condition. Using a 10 Td-s flash, there is no cutoff point where all the VTDR patients are on one side and healthy are on the other: the test does not have 100% sensitivity and specificity. In the example shown, 5 healthy individuals are classified as diseased and one of the diseased individuals is classified as healthy, leading to a sensitivity of 67% and a specificity of 30/35=86%. Using the 3.2 Td-s flash, the sensitivity is 100% and the specificity is 29/35=83%. Using both implicit times, shown as a solid line, provides a sensitivity is 100% and the specificity is 31/35=89%.

Example 3: Device and Device Test Protocol

For a second IRB-approved clinical trial, the device described in FIG. 1 and FIG. 2 was constructed. The device has the trade name RETeval (LKC Technologies, Gaithersburg, Md.). Using this device, a patient's eye may be visually stimulated. The pupil and electrical response were simultaneously recorded for four sets of flickering white light stimulation presented in randomized order. The four sets all had a flicker frequency of about 28.3 Hz with flash retinal illuminance energies of 4 Td·s, 8 Td·s, 16 Td·s, and 32 Td·s. Therefore, the average retinal illumination was 113 Td, 226 Td, 453 Td, and 906 Td. Results may be presented for the patient's right eye, left eye, both eyes, the best eye, or the worst eye. In the examples below, the patient's worst eye is used. Worst eye is defined as longer implicit times, smaller electrical amplitudes, and smaller pupil ratios. The implicit time from the electrical response was measured from the center of the flash of light to the peak of the electrical response. The commercially-available RETeval device did not analyze the pupil response to detect eye disease. The subjects were not artificially dilated.

Examples 4-7 use clinical trial data that was available at the time of filing a priority application U.S. 61/953,409. Examples 8 use all clinical trial data in the study.

Example 4: Results on Diabetic Patients without Retinopathy

Using 7 field stereo fundus photography with off-site non-physician expert graders (double-read with adjudication), 75 diabetics were identified as having no retinopathy (ETDRS score of 10) in both eyes.

The average of the square of the pupil diameters for the four retinal illuminations (from dimmest to brightest) was 10.3 $mm^2$, 7.96 $mm^2$, 5.94 $mm^2$, and 4.58 $mm^2$. The average ratio of the squares of the pupil diameters from the dimmest and brightest retinal illuminations was 2.23, with a standard deviation of 0.56.

The average implicit time from the electrical response for the four retinal illuminations (from dimmest to brightest) was 35.4 ms, 33.2 ms, 31.7 ms, and 30.1 ms. The implicit time from the brightest illumination had a standard deviation of 2.9 ms.

The average peak to peak amplitude of the electrical response for the four retinal illuminations (from dimmest to brightest) was 9.7 µV, 17.3 µV, 21.9 µV, and 24.5 µV. The standard deviation for the brightest retinal illumination was 9.1 µV.

Example 5: Results on a Patient with CRVO

One patient was identified as having central retinal vein occlusion (CRVO) on the same day as having the tests described in Example 1 performed.

The square of the pupil diameters for the four retinal illuminations (from dimmest to brightest) was 10.8 mm$^2$, 10.8 mm$^2$, 8.98 mm$^2$, and 9.28 mm$^2$. The average ratio of the squares of the pupil diameters from the dimmest and brightest retinal illuminations was 1.16. Using the signed-rank test of significance, this pupil ratio is statistically significantly smaller than the healthy population ($p=10^{-13}$). In fact, this pupil ratio is smaller than the smallest value obtained from the 75 patients without retinopathy.

The implicit time from the electrical response for the four retinal illuminations (from dimmest to brightest) was 36.1 ms, 33.5 ms, 32.2 ms, and 30.6 ms. Using the sign test of significance (a robust median test), these implicit times are statistically significantly larger than the healthy population ($p<10^{-7}$, $p<10^{-18}$, $p<10^{-17}$, $p<10^{-8}$, respectively from dimmest to brightest).

The peak-to-peak amplitude of the electrical response for the four retinal illuminations (from dimmest to brightest) was 36.7 ms, 35.6 ms, 34.3 ms, and 32.5 ms. Using the T test of significance, the amplitude from the brightest two retinal illuminations were statistically significantly smaller than the healthy population ($p<10^{-5}$ and $p<10^{-4}$, respectively from dimmest to brightest).

Example 6: Results on Diabetics with Severe Nonproliferative Diabetic Retinopathy or Proliferative Diabetic Retinopathy Forty-five diabetics with severe nonproliferative diabetic retinopathy or proliferative diabetic retinopathy, as determined from the fundus photography described above, were tested on the same day using the tests described in Example 1.

The area under the receiver operating characteristic curve (AUROC) was used to determine the performance of different analysis methods for distinguishing these diseased diabetics from those in Example 2 without retinopathy. For analyses using more than 1 measurement parameter, a logistic regression was used. Chance has an AUROC of 0.5.

Define P1, P2, P3, and P4 to be the pupil diameter from the 113 Td, 226 Td, 453 Td, and 906 Td average stimulus brightness, respectively. As examples, the following calculation may be made. Using P1/P4, (P1/P4)$^2$, or (P1−P4)/P4 the AUROC is 0.80. Using (P2−P4)/P4, (P2/P4)$^2$, or P2/P4, the AUROC is 0.72. Using (P3−P4)/P4, (P3/P4)$^2$, or P3/P4, the AUROC is 0.66. All are better than chance (AUROC=0.5). Many of these results are surprisingly good compared to the best of 9 metrics of pupil response measured by Straub et al (1992), which may be converted into a AUROC of 0.66 using equation (6) of Faraggi and Reiser (2002) assuming diseased and healthy individuals have independent normal variates. Straub et al (1992) did not use the novel stimulus techniques first disclosed in this specification.

Using the subjects' age and pupil information improved results. For example, using P1/P4, (P1/P4)$^2$, or (P1−P4)/P4 and age, both parameters were statistically significant ($p<0.05$) and the AUROC increased from 0.80 to 0.83. Using age by itself had an AUROC of 0.61. All are better than chance (AUROC=0.5).

Define T1, T2, T3, and T4 to be the implicit times from the electrical responses from the 113 Td, 226 Td, 453 Td, and 906 Td average stimulus brightness, respectively. The AUROC for T1, T2, T3, T4 are 0.65, 0.74, 0.75, and 0.78, respectively. Adding pupil information improved results for some combinations. For example, T4 and (P1/P4)$^2$ have an AUROC of 0.86 while T4 and (P2−P4)/P4 have an AUROC of 0.83. Another exemplary combination is T3 and (P1−P3)/P3, which has an AUROC of 0.79. Combining T4, (P1/P4)$^2$, and age has an AUROC of 0.90. All AUROCs are better than chance and all combinations described are statistically significant parameters.

Define A1, A2, A3, and A4 to be the peak to peak amplitudes from the electrical responses from the 113 Td, 226 Td, 453 Td, and 906 Td average stimulus brightness, respectively. Parameter A1 was not statistically significant ($p>0.05$). The AUROC for A2, A3, and A4 were 0.69, 0.71, and 0.67, respectively. Combining A4 with (P1/P4)$^2$ has an AUROC of 0.82. Combining A4, (P1/P4)$^2$, and age has an AUROC of 0.85. All AUROCs are better than chance and all combinations described (except A1) are statistically significant parameters.

Example 7: Results on Diabetics with Severe Nonproliferative Diabetic Retinopathy or Proliferative Diabetic Retinopathy or Clinically Significant Macular Edema Eighty diabetics having at least one of the following conditions as determined from the fundus photography described above, were tested on the same day using the tests described in Example 1: clinically significant macular edema, severe nonproliferative diabetic retinopathy or proliferative diabetic retinopathy.

The area under the receiver operating characteristic curve (AUROC) was used to determine the performance of different analysis methods for distinguishing these diseased diabetics from those in Example 2 without retinopathy. For analyses using more than 1 measurement parameter, a logistic regression was used. Chance has an AUROC of 0.5.

Define P1, P2, P3, and P4 to be the pupil diameter from the 113 Td, 226 Td, 453 Td, and 906 Td average stimulus brightness, respectively. As examples, the following calculation may be made. Using P1/P4, (P1/P4)$^2$, or (P1−P4)/P4 the AUROC is 0.79. Using (P2−P4)/P4, (P2/P4)$^2$, or P2/P4, the AUROC is 0.71. Using (P3−P4)/P4, (P3/P4)$^2$, or P3/P4, the AUROC is 0.63. All are better than chance (AUROC=0.5).

Using the subjects' age and pupil information improved results. For example, using P1/P4, (P1/P4)$^2$, or (P1−P4)/P4 and age, both parameters were statistically significant ($p<0.05$) and the AUROC increased from 0.79 to 0.81. Using age by itself had an AUROC of 0.62. All are better than chance (AUROC=0.5).

Define T1, T2, T3, and T4 to be the implicit times from the electrical responses from the 113 Td, 226 Td, 453 Td, and 906 Td average stimulus brightness, respectively. The AUROC for T1, T2, T3, T4 are 0.64, 0.72, 0.71, and 0.75, respectively. Adding pupil information improved results for some combinations. For example, T4 and (P1/P4)$^2$ have an AUROC of 0.83 while T4 and (P2−P4)/P4 have an AUROC of 0.83. Another exemplary combination is T3 and (P1−P3)/P3, which has an AUROC of 0.80. Combining T4, (P1/P4)$^2$, and age has an AUROC of 0.86. All AUROCs are better than chance and all combinations described are statistically significant parameters.

Define A1, A2, A3, and A4 to be the peak to peak amplitudes from the electrical responses from the 113 Td, 226 Td, 453 Td, and 906 Td average stimulus brightness, respectively. Parameter A1 was not statistically significant ($p>0.05$). The AUROC for A2, A3, and A4 were 0.67, 0.70, and 0.67, respectively. Combining A4 with (P1/P4)$^2$ has an AUROC of 0.82. Combining A4, (P1/P4)$^2$, and age has an AUROC of 0.84. All AUROCs are better than chance and all combinations described (except A1) are statistically significant parameters.

Example 8: Results on Diabetics with Varying Levels of Diabetic Retinopathy

A total of 467 diabetics completed the study. Using 7 field stereo fundus photography with off-site non-physician expert graders (double-read with adjudication), as the gold standard, subjects were classified as to the extent of diabetic retinopathy in their worst eye. The table below shows the number of subjects in each category.

| International Classification of Diabetic Retinopathy | ETDRS Level | CSME | n | % |
|---|---|---|---|---|
| No NPDR | 10-12 | − | 93 | 20 |
| Mild NPDR | 14-35 | − | 127 | 27 |
| Moderate NPDR | 43-47 | − | 90 | 19 |
| None, Mild or Moderate | 10-47 | + | 39 | 8 |
| Severe or Proliferative | 53-85 | ± | 52 | 11 |
| Ungradable ETDRS Level | ? | + | 15 | 3 |
| Ungradable photographs | ? | ? | 51 | 11 |
| | | Total | 467 | |

Figure 5A:
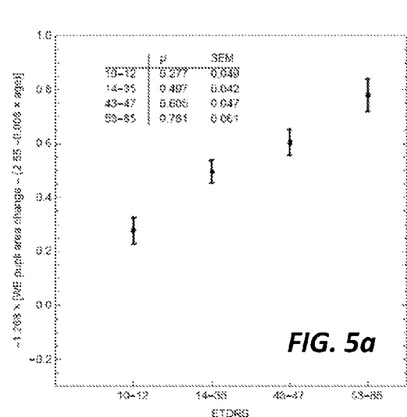
FIG. 5 shows exemplary clinical data. The x-axes shows 4 diabetic retinopathy groupings. ETDRS levels 10-12 represent diabetics with no non-proliferative diabetic retinopathy (NPDR). ETDRS levels 14-35 represent diabetics with mild NPDR. ETDRS 43-47 represent diabetics with moderate NPDR. ETDRS 53-85 represent diabetics with severe NPDR or proliferative diabetic retinopathy (PDR). The y-axes represent measurements or combinations of measurements from an exemplary device. The points represent the mean and the error bars are ±1 standard error of the mean.

FIG. 5a shows the how diabetic retinopathy affects the measured pupil response $(P1/P4)^2$ (as defined in Example 7), after correcting for the dependence on age as determined by the no NPDR subjects. Diabetic retinopathy has statistically significant effect pupillary response with 2.9 standard errors of the mean separating the severe or proliferative subjects from those with moderate NPDR.

Figure 5B:
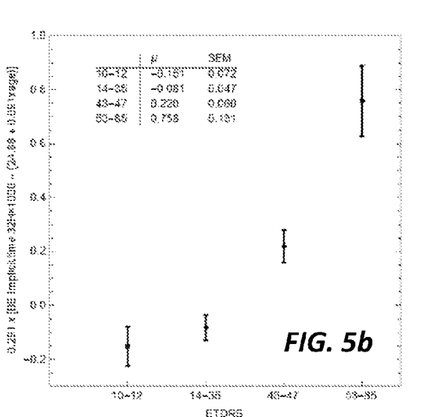

FIG. 5b shows the how diabetic retinopathy affects the measured implicit time (time from the flash to the peak electrical response) from the electrical response from the 32 Td·s, 28.3 Hz flicker stimulus (average retinal illuminance of 906 Td), after correcting for the dependence on age as determined by the no NPDR subjects. Diabetic retinopathy has statistically significant effect pupillary response with 4.1 standard errors of the mean separating the severe or proliferative subjects from those with moderate NPDR.

Figure 5C:
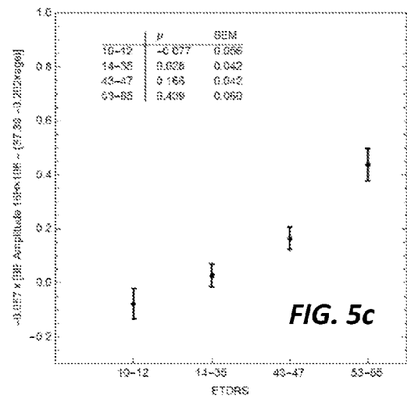

FIG. 5c shows the how diabetic retinopathy affects the peak-to-peak amplitude from the electrical response from the 16 Td·s, 28.3 Hz flicker stimulus (average retinal illuminance of 453 Td), after correcting for the dependence on age as determined by the no NPDR subjects. Diabetic retinopathy has statistically significant effect pupillary response with 4.6 standard errors of the mean separating the severe or proliferative subjects from those with moderate NPDR.

Figure 5D:
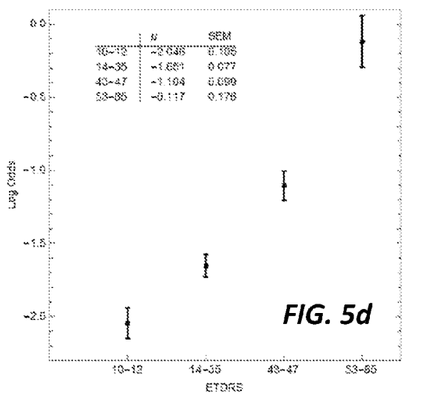

FIG. 5d shows the how diabetic retinopathy affects the log odds of a logistic regression fit of the (age corrected) pupillary response $(P1/P4)^2$, peak-to-peak amplitude from the electrical response from the 16 Td·s, 28.3 Hz flicker stimulus, implicit time from the electrical response from the 32 Td·s, 28.3 Hz flicker stimulus. The log odds equals the sum of the terms plotted in FIGS. 4a-4c. Diabetic retinopathy has statistically significant effect on the logistic regression log odds with 5.6 standard errors of the mean separating the severe or proliferative subjects from those with moderate NPDR. The log odds has an AUROC of 0.88 when VTDR is defined as severe NPDR or PDR. The log odds has an AUROC of 0.86 when VTDR is defined as having at least one of severe NPDR, PDR, or CSME.

All references cited herein are incorporated by reference in their entirety. To the extent publications and patents or patent applications incorporated by reference contradict the disclosure contained in the specification, the specification is intended to supersede or take precedence over any such contradictory material.

All numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description of devices includes many novel and advantageous aspects. Combinations of the aspects are also contemplated. It will be apparent to those skilled in the art that various modifications and variations may be made in the disclosed detection device, components, and methods without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims and their equivalents.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

CITED REFERENCES

AAO. "Preferred Pracitice Pattern for Diabetic Retinopahty." *American Academy of Ophthalmology*, 2003: 1-36.

Aiello L P, Gardner T W, King G L, Blankenship G, Cavallerano J D, Ferris F L, Klein R. (1998) Diabetic retinopathy. Diabetes Care 21:143-156.

Antonetti D A, Barber A J, Bronson S K, Freeman W M, Gardner T W, Jefferson L S, Kester M, Kimball S R, Krady J K, Lalloue K F, Norbury C C, Quinn P G, Sandirasegarane L, Simpson I A, Grp JDRC. (2006) Diabetic retinopathy—Seeing beyond glucose-induced microvascular disease. *Diabetes* 55:2401-2411

Bresnick, George, and Mari Palta. (1987) "Temporal Aspects of the Electroretinogram in Diabetic Retinopathy." Arch Opthalmol, 105:660-4.

Devos A, Marcus J T, Reulen J P H, Peters H F M, Heimans J J, Vanderveen E A (1989) The pupillary light reflex in diabetes-mellitus—Evaluation of a newly developed infrared light-reflection method. *Diabetes Research Clinical and Experimental* 10:191-195.

Faraggi D and Reiser B (2002) "Estimation of the area under the ROC curve." *Statistics in Medicine* 21:3093-3106.

Han, Young-Keun, and Young-Hoon Ohn. (2000) "Changes of ERG Parameters in Diabetic Retinopathy." J Korean Ophthalmol Soc, 41:149-155.

Hreidarsson A B (1982) Pupil size in insulin-dependent diabetes. Relationship to duration, metabolic control, and long-term manifestations. *Diabetes* 31:442-448.

Holder, Graham, et al. (2007) "ISCEV standard for clinical pattern electroretinography—2007 update." *Doc Ophthalmol*, 114:111-116.

Hood, Donald, et al. (2012) "ISCEV standard for clinical multifocal electroretinography (mfERG) (2011 edition)." *Doc Ophthalmol*, 124:1-13.

Kjeka, O, R W Jansson, C Bredru, and J Krohn. (2013) "Early panretinal photocoagulation for ERG-verified ischaemic central retinal vein occlusion." *Acta Ophthalmol*, 37-41.

Kuroda N, Taniguchi H, Baba S, Yamamoto M. (1989) Pupillary light reflex in borderline diabetes-mellitus. *Diabetes Research and Clinical Practice* 6:89-94.

Marmor, M F, et al. (2009) "ISCEV standard for full-field clinical electroretinography (2008 update)." *Doc Ophthalmol*, 118:69-77.

Odom, Vernon, et al. (2010) "ISCEV standard for clinical visual evoked potentials. (2009 update)." *Doc Ophthalmol*, 120:111-119.

Satoh, S, H Iljma, M Imai, K Abe, and T Shibuya. (1994) "Photopic electroretinogram implicit time in diabetic retinopathy." *Japanese Journal of Ophthalmology*, 38: 178-184.

Severns, M L, Johnson, M A and Merritt, S A. (1991) "Automated estimate of implicit time and amplitude of the flicker electroretinogram." *Applied Optics* 30:2106-2112.

Severns, M L and Johnson, M A (1991) "Automated implicit time and amplitude determination for the 30 Hz flicker electroretinogram: performance prediction of neovascularization central retinal vein occlusion." *Technical Digest Series*, Washington, D.C.; Optical Society of America, pp. 10-13.

Severns, M L and Johnson, M A (1993) "Predicting Outcome in Central Retinal Vein Occlusion Using the Flicker Electroretinogram." *Arch Ophthalmol* 111:1123-1130.

Schwartz S G, Flynn H W (2007) Pharmacotherapies for Diabetic Retinopathy: Present and Future. *Experimental Diabetes Research*.

Straub R H, Jeron A, and Kerp L (1992). "The Pupillary Light Reflex." *Ophthalmoligica* 204:143-148.

Straub R H, et al. (1994). "Valid Parameters for Investigation of the Pupillary Light Reflex in Normal and Diabetic Subjects shown by Factor Analysis and Partial Correlation." *Diabetoligia* 37:414-419.

Wilkinson C P, et al. (2003) "Proposed International Clinical Diabetic Retinopathy and Diabetic Macular Edema Disease Severity Scales." *Ophthalmology*, 110:1677-1682

What is claimed is:

1. A device providing an indication of eye disease in a patient comprising:
   a. a light emitter;
   b. an optical assembly arranged so that light emitted from the light emitter reaches an eye of the patient in a diffuse manner;
   c. a camera arranged to image the eye of the patient; and
   d. a controller;
   wherein the controller measures the eye's pupil area using images received from the camera and adjusts luminance of the light emitted from the light emitter as a non-constant function of the eye's pupil area so as to create at least two stimulus intervals,
   wherein the at least two stimulus intervals have different, nonzero, average retinal illuminances,
   wherein at least one of the at least two stimulus intervals has a stimulus frequency between 4 Hz and 50 Hz, and
   wherein the controller analyzes pupil measurements in the at least two stimulus intervals and provides the indication of eye disease based on that analysis.

2. The device of claim 1, wherein the at least two stimulus intervals comprise flashes of light having a flash frequency between 4 Hz and 50 Hz and having retinal illuminance energies that are within a factor of 1.2 of one of 1, 2, 4, 8, 10, 16, and 32 Troland times second (Td·s).

3. The device of claim 1, wherein
   the at least two stimulus intervals comprise flashes of light having a flash frequency between 20 Hz and 40 Hz;
   the at least two stimulus intervals include a first stimulus interval whose average retinal illuminance is between 10 Td and 200 Td and a second stimulus interval whose average retinal illuminance is between 400 Td and 2000 Td;
   the first stimulus interval occurs before the second stimulus interval;
   the first stimulus interval comprises flashes of light having retinal illuminance energies within a factor of 1.2 of 4 Td·s; and
   the second stimulus interval comprises flashes of light having retinal illuminance energies within a factor of 1.2 of 32 Td·s.

4. The device of claim 1, wherein the controller receives and analyses both the pupil measurements and an electrical signal from a visual system of the patient and wherein the indication is based on analysis of the electrical signal and the pupil measurements.

5. The device of claim 4, wherein there is at least one of the at least two stimulus interval whose pupil measurements and electrical signals are both used in the analysis for the indication of eye disease.

6. The device of claim 5, wherein the indication of eye disease is also dependent of the patient's age.

7. The device of claim 6, wherein the eye disease is retinitis, optic neuritis, macular degeneration, diabetic retinopathy, proliferative diabetic retinopathy, nonproliferative diabetic retinopathy, diabetic macular edema, progressive retinal atrophy, progressive retinal degeneration, sudden acquired retinal degeneration, immune-mediated retinopathy, retinal dysplasia, chorioretinitis, retinal ischemia, retinal hemorrhage, hypertensive retinopathy, retinal inflammation, retinal edema, retinoblastoma, central retinal vein occlusion, branch retinal vein occlusion, or retinitis pigmentosa.

8. The device of claim 7, wherein the eye disease is diabetic retinopathy or diabetic macular edema.

9. The device of claim 1, wherein the stimulus frequency is within 0.1 Hz of one of the following frequencies: 28.31, 28.72, or 32.55, or integer multiples thereof.

10. A device providing an indication of eye disease in a patient comprising:
    a. an illumination system configured to provide an eye of the patient with at least two stimulus intervals of flashes of light that differ in at least one property, and the at least one property is selected from flash frequency, flash color, background retinal illuminance, background color, and retinal illuminance energy;
    b. a controller adapted to receive and analyze an electrical signal from a visual system of the patient from at least two stimulus intervals of flashes of light so as to provide the indication of eye disease based on that analysis;
    wherein the flash frequencies of the at least two stimulus intervals are between 4 Hz and 50 Hz; and wherein the retinal illuminance energies of the at least two stimulus intervals are within a factor of 1.2 of one of 1, 2, 4, 8, 10, 16, and 32 Td·s.

11. The device of claim 10, wherein the illumination system comprises
   a. a light emitter;
   b. an optical assembly arranged so that light emitted from the light emitter reaches the eye of the patient in a diffuse manner; and
   c. a camera arranged to image the eye of the patient;
   wherein the controller measures the eye's pupil area using images received from the camera and adjusts luminance of the light emitted from the light emitter as a non-constant function of the eye's pupil area so as to create a plurality of the at least two stimulus intervals,
   wherein the at least two stimulus intervals have different, nonzero, average retinal illuminances, and
   wherein the controller analyzes pupil measurements in the at least two stimulus intervals and provides the indication of eye disease based on the combination of the electrical signal analysis and the pupil measurements analysis.

12. The device of claim 11, wherein the flash frequencies of the at least two stimulus intervals are between 20 Hz and 40 Hz.

13. The device claim 10, wherein the background retinal illuminance for at least one of the at least two stimulus intervals is 0.

14. The device of claim 10, wherein the flash frequencies are within 0.1 Hz of one of the following frequencies: 28.31, 28.72, or 32.55, or integer multiples thereof.

15. A method for providing an indication of eye disease in a patient comprising:
   illuminating an eye of the patient with a diffuse light stimulus having at least two stimulus intervals having different, nonzero, average retinal illuminances wherein at least one of the at least two stimulus intervals has a stimulus frequency between 4 Hz and 50 Hz;
   measuring the eye's pupil area and adjusting luminance of the diffuse light as a non-constant function of the eye's pupil area; and
   providing the indication of eye disease based on pupil measurements.

16. The method of claim 15, wherein the at least two stimulus intervals comprise flashes of light having flash frequencies between 4 Hz and 50 Hz and having retinal illuminance energies that are within a factor of 1.2 of one of 1, 2, 4, 8, 10, 16, and 32 Td·s.

17. The method of claim 16, wherein
   the at least two stimulus intervals comprise flashes of light having flash frequencies between 20 Hz and 40 Hz;
   the at least two stimulus intervals include a first stimulus interval whose average retinal illuminance is between 10 Td and 200 Td and a second stimulus interval whose average retinal illuminance is between 400 Td and 2000 Td;
   the first stimulus interval occurs before the second stimulus interval;
   the first stimulus interval comprises flashes of light having retinal illuminance energies within a factor of 1.2 of 4 Td·s; and
   the second stimulus interval comprises flashes of light having retinal illuminance energies within a factor of 1.2 of 32 Td·s.

18. The method of claim 15, further comprising receiving and analyzing an electrical signal from a visual system of the patient and wherein the indication is based on analysis of the electrical signal and the pupil measurements.

19. The method of claim 18, wherein there is at least one of the at least two stimulus interval whose pupil measurements and electrical signals are both used in the analysis for the indication of eye disease.

20. The method of claim 19, wherein the indication of eye disease is also dependent of the patient's age.

21. The method of claim 15, further comprising receiving and analyzing an electrical signal from a visual system of the patient from each interval,
   wherein:
   the at least two stimulus intervals comprise at least three stimulus intervals having the same flash frequency between 20 Hz and 40 Hz, each of the at least three stimulus intervals having a retinal illuminance energy within a factor of 1.2 of one of 4, 16, and 32 Td·s,
   the indication of eye disease is also dependent of the patient's age,
   the indication is based on analysis of the electrical signal and the pupil measurements, and
   the patient has not been artificially dilated.

22. A method for providing an indication of eye disease in a patient comprising:
   illuminating an eye of the patient with at least two stimulus intervals of flashes of light that differ in at least one property, and the at least one property is selected from flash frequency, flash color, background retinal illuminance, background color, and retinal illuminance energy;
   receiving and analyzing an electrical signal from a visual system of the patient from each of the at least two stimulus intervals so as to provide the indication of eye disease based on the electrical signals;
   wherein the flash frequencies of the at least two stimulus intervals are between 4 Hz and 50 Hz; and
   wherein the retinal illuminance energies of the at least two stimulus intervals are within a factor of 1.2 of one of 1, 2, 4, 8, 10, 16, and 32 Td·s.

23. The method of claim 22, wherein the eye disease is retinitis, optic neuritis, macular degeneration, diabetic retinopathy, proliferative diabetic retinopathy, nonproliferative diabetic retinopathy, diabetic macular edema, progressive retinal atrophy, progressive retinal degeneration, sudden acquired retinal degeneration, immune-mediated retinopathy, retinal dysplasia, chorioretinitis, retinal ischemia, retinal hemorrhage, hypertensive retinopathy, retinal inflammation, retinal edema, retinoblastoma, central retinal vein occlusion, branch retinal vein occlusion, or retinitis pigmentosa.

24. The method of claim 22, wherein the eye disease is diabetic retinopathy or diabetic macular edema.

25. The method of claim 22, further comprising receiving and analyzing pupil measurements from the patient from each of the at least two stimulus intervals, wherein:
   the at least two stimulus intervals comprise at least three stimulus intervals having the same flash frequency between 20 Hz and 40 Hz, each of the at least three stimulus intervals having the retinal illuminance energy within a factor of 1.2 of one of 4, 16, and 32 Td·s,
   the indication of eye disease is also dependent of the patient's age,
   the indication is based on analysis of the electrical signal and the pupil measurements, and
   the patient has not been artificially dilated.

* * * * *